United States Patent [19]

Groiso

[11] Patent Number: 5,660,188

[45] Date of Patent: Aug. 26, 1997

[54] PROCEDURE FOR APPLYING AN ELASTIC CLIP

[76] Inventor: Jorge A. Groiso, Ayacucho 1570 P. 9, Buenos Aires 1112, Argentina

[21] Appl. No.: 453,905

[22] Filed: May 30, 1995

Related U.S. Application Data

[62] Division of Ser. No. 231,993, Apr. 21, 1994, Pat. No. 5,449,359, which is a continuation of Ser. No. 48,076, Apr. 15, 1993, abandoned, which is a continuation of Ser. No. 803,491, Dec. 4, 1991, abandoned.

[30] Foreign Application Priority Data

May 9, 1991 [AR] Argentina ................. 320.597

[51] Int. Cl.⁶ .................................................. A61B 19/00
[52] U.S. Cl. ...................... 128/898; 606/75; 606/63; 606/60
[58] Field of Search ................... 606/74, 75, 60, 606/63, 212; 128/898

[56] References Cited

U.S. PATENT DOCUMENTS

| | | | |
|---|---|---|---|
| 4,146,022 | 3/1979 | Johnson et al. | 606/74 |
| 4,444,181 | 4/1984 | Wevers et al. | 606/75 |
| 4,512,346 | 4/1985 | Lemole | 606/74 |
| 4,887,601 | 12/1989 | Richards | 606/219 |
| 5,324,307 | 6/1994 | Jarrett et al. | 606/219 |
| 5,449,359 | 9/1995 | Groiso | 605/75 |

FOREIGN PATENT DOCUMENTS 3412769  10/1985  Germany ................. 606/74

*Primary Examiner*—Paul B. Prebilic
*Attorney, Agent, or Firm*—Ostrolenk, Faber, Gerb & Soffen, LLP

[57] ABSTRACT

An elastic clip for osteosynthesis for connecting at least two bone parts together, comprising a body having at least two spaced legs, each leg having a lower end which can be inserted into a bone part and each having an upper end, the upper ends of said at least two legs being attached to corresponding ends of an elastic bridge which is deformable by pressure and which preferably comprises at least two elongated sections which extend alongside each other. Preferably, the clip has four legs attached in pairs to each of the ends of the bridge, the legs of each pair being attached together. The two elongated sections have at least a portion where they are not connected together, so that the two bridge sections can be forced apart to hold the bone parts in place. Alternatively, the two bridge sections are spaced apart and brought together to hold two bone parts together with a prescribed spacing.

4 Claims, 2 Drawing Sheets

PROCEDURE FOR APPLYING AN ELASTIC CLIP

This is a division of application Ser. No. 08/231,993, filed Apr. 21, 1994 and now U.S. Pat. No. 5,449,359, which is in turn a continuation of Ser. No. 08/048,076 filed Apr. 15, 1993 and now abandoned, which is in turn a continuation of Ser. No. 07/803,491 filed Dec. 4, 1991 and now abandoned.

BACKGROUND OF THE INVENTION

The present invention relates to the consolidation (cicatrization) between bone parts in which it is necessary to maintain the parts together for the duration of the process of union between them. Furthermore, the present invention also permits two parts of a bone to consolidate properly, correcting any tendency towards malformation thereof. More particularly, the present invention relates to a clip for osteosynthesis having elastic properties, and it also relates to the method and the instrument for the placing thereof.

Various elements are known which permit the cicatrization of two bone parts or fragments by holding them together and avoiding their movement insofar as possible. Thus, there are external elements such as casts and internal elements such as screws, plates, clips, etc. which perform the same function. Argentine Patent 203,977 refers to a curved nail for the treatment of fractures, it comprising an elongated body which at one end has a coupling part which is to be inserted into the bone. Types of plates and nails for the knitting of femur heads are known from Patent 212,889 and Patent 214,240. Connecting plates for two fragments of bones are also known from Argentine Patent 211,803 in which a plate with orifices for screws is placed over the parts to be connected.

Argentine Patent No. 236,884 refers to a fastening clip especially for osteosynthesis and, for its application, the clip must be inserted in the bone by at least one pair of legs while a bridge portion which connects the two legs together remains outside the bone and effects the connection between the two bone fragments. This clip is to be used especially together with a similar clip, each one placed on each adjacent portion of bone to be connected; the bridge portions of the two clips are then connected together by an elastic element which pulls the two bone parts together that are being united.

Although some of the known embodiments have given generally good results, the doctor is confronted with the problem that some connecting elements are bulky and complicated, which increases the traumatic suffering to which the patient is subjected and the smaller ones, like clips, once placed, do not succeed in efficiently fastening the bone portions together, it not being possible to avoid that one bone part turns with respect to the other or shifts. When it is desired to consolidate two bone fragments, it is necessary to have excellent contact between the parts as well as compression between bone ends. Scientific investigations have shown that by suitable compression between the parts to be connected, a faster consolidated of better quality is obtained.

Since, in order to place the parts to be connected in contact and fix them, it is necessary to work through the wound of the patient, it is preferred that the connecting means be as simple as possible. Therefore, those internal connecting elements which comprise plates and screws are not to be recommended, particularly in the case of simple fractures.

In order to avoid the foregoing, there are simple clips of U-shape which are very similar to those clips which are used in paper staplers. These U-shaped clips have their ends which are inserted in a bone portion sharpened and they maintain their position by the rigid structure of the legs of the U. However, these conventional clips maintain the same distance between the bone fragments and, therefore, if there is not coaptation, there is instability in rotation, which means that the bone portions-may turn with respect to each other and may even separate. This phenomenon would not occur if one succeeded in maintaining the bone ends compressed against each other.

For the contrary case, in which it is desired to maintain a force of separation between the bone fragments, which case is particularly useful for bone malformation connection, there are no clips which make it possible to obtain this spacing and, therefore, it would be very useful to have clips which make it possible to achieve this.

As stated above, this could be obtained by connecting elements such as plates and screws, but these are much bulkier and require major surgical procedures for the placing thereof.

SUMMARY OF THE INVENTION

It is an object of the present invention to provide an elastic clip for osteosynthesis which solves the problems mentioned above, that is to say, avoids that once the clip is put in place, the bone fragments move with respect to each other and, on the other hand, are maintained compressed by means of their connected ends without the necessity of complicated and bulky parts which would require traumatic major surgical procedures.

A further object of the present invention is to provide a procedure for osteosynthesis by use of the elastic clip of the present invention, the procedure comprising simple steps which avoid subjecting the patient to traumatic conditions and facilitate the placing on of the clip.

Another object of the present invention is to provide an instrument for the placing on of the elastic clip of the present invention which facilitates the placing work and the effectiveness of the connection of the bone portions, making it possible to obtain the desired compression or expansion between them.

Still another object of the present invention is to provide an elastic clip for osteosynthesis for the connecting of at least two bone fragments, which comprises a body formed by at least two spaced legs, each of which has a lower end which can be inserted into the bone and an upper end, the upper ends of said at least two legs being connected to the two ends of an elastic bridge deformable by pressure which comprises at least two elongated portions which extend alongside of each other.

Still another object of the present invention is to provide a procedure for the connecting of at least two bone fragments by the application of the clip of the invention, which comprises the steps of:

placing the parts of the bone to be connected opposite each other;

effecting drillings in the parts in order for each of them to receive one of the legs of the clip;

placing the clip on by inserting each leg into each perforation and fastening the leg within the perforation; and deforming the elongated sections of the bridge of the clip by pressure.

It is also an object of the present invention to provide an instrument for the placing on of the clip of the invention which comprises a forceps which has a handle part and a forceps part which has a nose which can be inserted between the portions.

Other features and advantages of the present invention will become apparent from the following description of the invention which refers to the accompanying drawings.

BRIEF DESCRIPTION OF THE DRAWINGS

For greater clarity and understanding, the present invention has been shown in various figures in which it is illustrated in its preferred embodiments, all by way of illustration and not of limitation, and in which we see that.

DETAILED DESCRIPTION OF THE DRAWINGS

Figure 1:
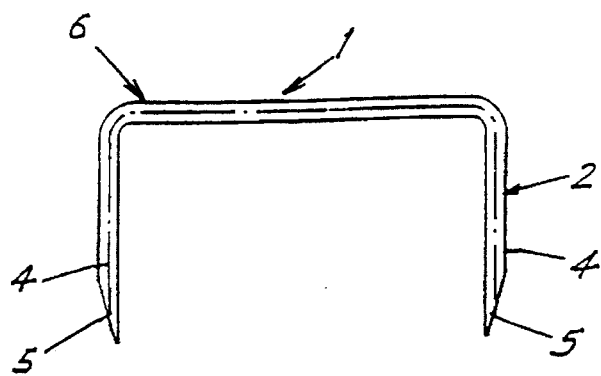
FIG. 1 is a side elevation of a preferred embodiment of the clip of the invention.

Referring to the figures, it should be pointed out that in the different embodiments, the reference numbers used in FIG. 1 will be used for equivalent parts of the embodiments of the different figures with the same digit but increased by 10. Thus, the embodiment of FIG. 1 will be identified by the number 1 while the following embodiments of FIGS. 4 and 7 will bear the numbers 11 and 21.

Figure 2:
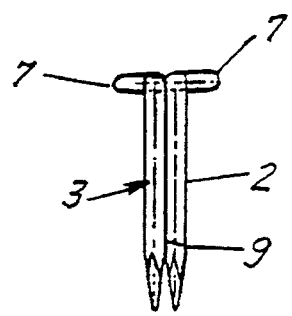
FIG. 2 is a front view in elevation of the clip of FIG. 1.
Figure 3:
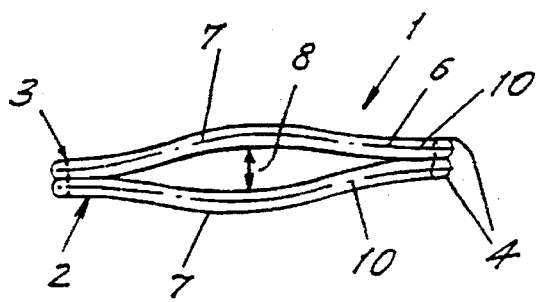
FIG. 3 is a plan view from above the clip of FIG. 1.

Referring to FIG. 1, there can be noted the elastic osteo-synthesis clip in accordance with the present invention seen in a side view. As appears more clearly from viewing FIGS. 1, 2 and 3 together, the clip 1 is formed of two similar clip pieces 2 and 3 placed face to face, each of which has a substantially inverted U-shape with vertical legs 4 and a substantially horizontal portion 6 referred to as bridge.

The legs 4 which are intended to be inserted into the ends of the bone fragments to be connected will probably have their ends 5 sharpened so as to facilitate the insertion of the legs into the body of the bone.

The bridge 6 will constitute a deformable elastic bridge due to the construction of the clip 1. In fact, the adjacent legs 4, that is to say, the legs of the clip piece 2 and of the clip piece 3 which are arranged alongside each other will be duly attached together, for instance, by extensive welding along the connecting line 9, while the bridge 6 will be formed of two elongated sections 10 which extend one alongside of each other and which, in the case of the embodiment of FIG. 1, have a bulge 7 which defines a space or separation 8 between the elongated sections 10. As will be seen subsequently when referring to the method of the present invention, the space 10 will make it possible to utilize the elasticity of the elongated sections 10 of the bridge 6 in order to put into practice those characteristics of the invention which lead to a suitable connection between ends of the bone fractions to be consolidated or else generates a suitable force of separation.

In accordance with the preferred embodiment, the clip parts 2 and 3 will be formed of metal bars of circular cross section, which will facilitate their introduction into the pieces of bone, as well as their elastic working during application and use. The legs 4 will preferably be polished in order to facilitate sliding within the orifice previously drilled in the bone and, as stated previously, the ends 5 will be suitably sharpened in order further to facilitate this insertion.

The clip will preferably be made of a biocompatible material which is of good elasticity and good mechanical strength. Materials of this type which are suitable for use in the present invention are, for instance, a titanium alloy metal such as TA6V of medical grade. The end legs 4 will preferably extend parallel to each other within the same clip whether 2 or 3 and, furthermore, the legs 4 of the clip piece 2 will also extend parallel to the legs 4 of the clip piece 3.

Reference will be had below to the procedure of the present invention for the connecting of at least two bone fragments by the application of the clip of the present invention. In the description of the procedure, reference will be had to the embodiment of FIG. 1, it being understood that this procedure may be carried out with any of the embodiments to which reference will be had further below.

Figure 10:
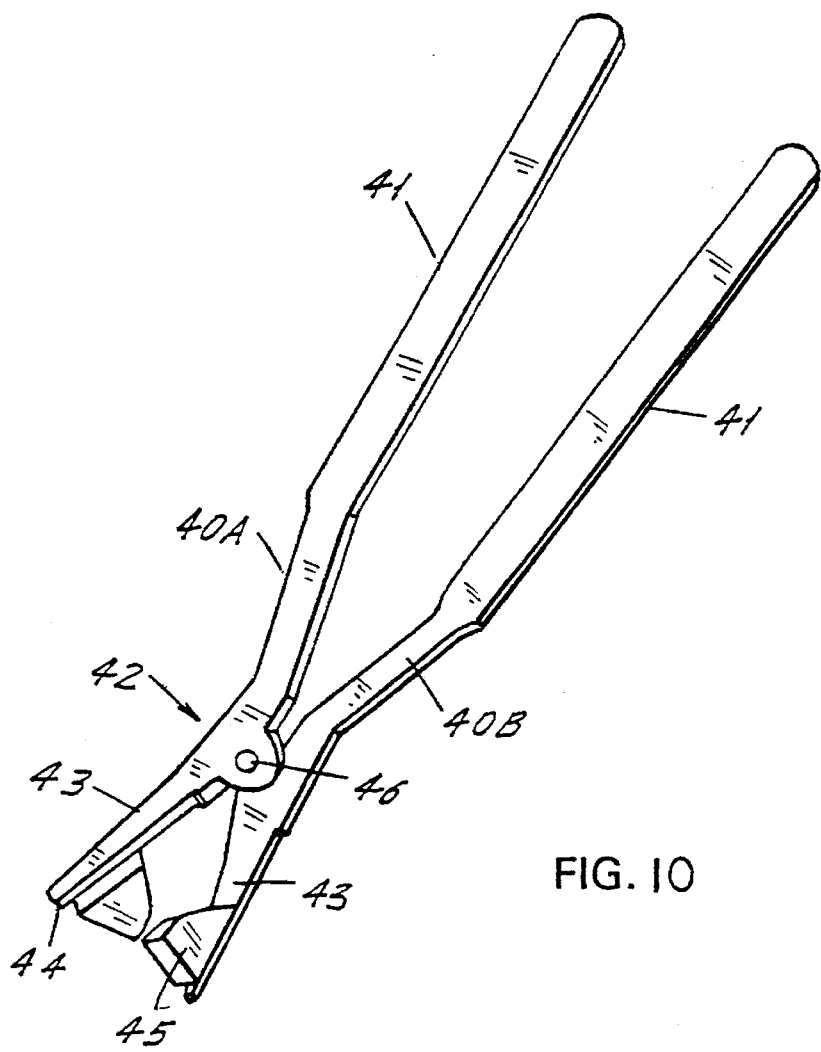
FIG. 10 is a diagrammatic illustration of a clip-placing element of the present invention, showing the instrument closed.

During the carrying out of the procedure, the bone fragments to be connected must be drilled at the places at which the legs 4 are to be inserted. Once at least the ends of the legs 4 have been inserted, the clip is grasped by an instrument 40, shown in FIG. 10, to which reference will be had further below, and, by means of a suitable percussion tool, the instrument is struck, pushing the clip 1 until the bridge 6 comes into contact with the outer surface of the bone. Once in this position, the elongated sections 10 are separated by the tool 40 which causes an increase in the space 8 and, as a result of this, the legs 4 of one end approach the legs 4 of the other end, carrying the bone pieces along with them and causing the ends of the bone fragments to come in contact under pressure. It has been shown that the bone consolidation of a fracture is impossible, or almost impossible, if there are movements in rotary direction of the bones which avoid the fracture surface of the bone pieces being maintained in contact. However, it has also been shown scientifically that it is not advisable to maintain the two contacting fracture surfaces completely rigid since the consolidation is effected more favorably when the contact pressure between the two surfaces is variable and not excessive. With the clip of the present invention, the bone ends connected will be maintained under pressure due to the pulling together of the legs 4 of each end of the clip 1, which is obtained by the elastic traction obtained by the separating of the elongated section 10 of the deformable elastic bridge 6.

In contrast to the prior application, the clip of the present invention is also used in applications where it is necessary to maintain a force of separation between the bone ends to be connected. This is necessary in some cases in which a correction is desired in a bone piece which otherwise would consolidate and even grow in a manner other than that desired. The procedure of the invention in this case will be carried out by placing the clip in the bone pieces as described previously, but instead of separating the elongated sections 10 the widened portions 7 of the elongated sections 10 are compressed so as to produce a movement apart between the legs 4 of the ends of the clip 1.

In order to produce the separation between the elongated ends 10, the present invention provides an instrument 40 which has a handle part 41 and a nose part 42 which comprises two separable jaws 43, the end 44 of which is intended to be inserted between the elongated sections 10 and, particularly, within the space 8. The jaws 43 each include a protrusion 45 intended to rest against the clip 10 and allow the wedging of the end 44 within the space 8. The protrusion 45, upon resting against the bridge 6 of the clip, will also make it possible, upon striking the tool 40, for the legs 4 to be introduced into the orifices of the bone fragments. The forceps 40 will be formed of a part 40a and a part 40b, the two parts being articulated by a pivot pin 46 so that when the handle parts 4 are squeezed, the jaws 43 move away from each other so that, when within the space 8, they cause the opening of the clip 1 in order to obtain the results to which reference has been had above when describing the procedure.

Figure 4:
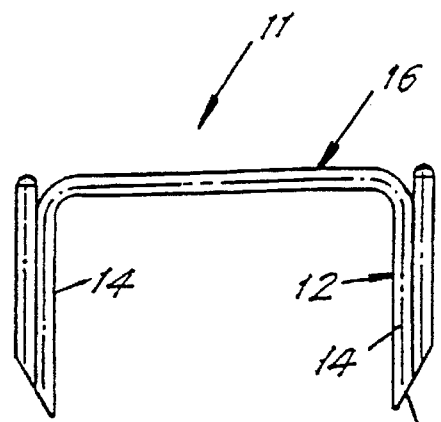
FIG. 4 illustrates another embodiment of the clip of the invention seen in a side elevation.
Figure 5:
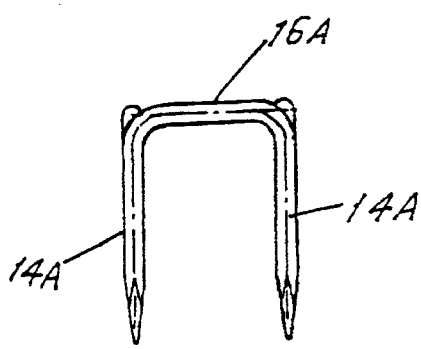
FIG. 5 is a front view in elevation of the clip of FIG. 4.
Figure 6:
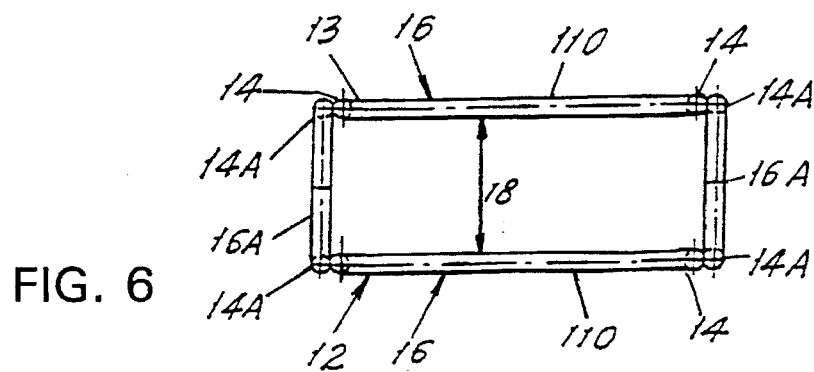
FIG. 6 is a top plan view of the clip of FIG. 4.

Referring now to FIGS. 4 to 6, these figures illustrate a second embodiment which consists of a clip 11 formed of two clip pieces 12 and 13, each of which has legs 14 and a bridge 16, the bridge 16 being formed by elongated bridge sections 110. Differing form the embodiment of FIG. 1, the clip pieces 12 and 13 are attached to each other by an intermediate clip part at each end. The intermediate parts are clip parts formed by a bridge portion 16a and legs 14a. The legs 14a of the intermediate clip part will be attached to the legs 14 of the parts 12 and 13. The use of this clip is identical in concept to the use of the clip of the preceding embodiment. In view of the separation between the legs 14, the stability of this clip will be greater than that of the clip in FIG. 1 but it will operate in the same manner since separation between the elongated sections 110 or else their compression will also be effected in order to modify the space 18. The ends of the connected legs 14 and 14a also will be beveled or sharpened as indicated by the reference numeral 15 in order to facilitate the insertion thereof into the corresponding bone piece.

Figure 7:
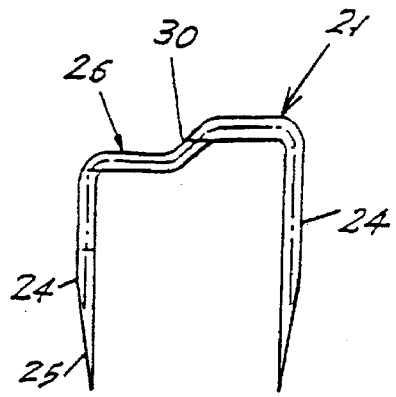
FIG. 7 illustrates another embodiment of the clip of the invention in a side elevation.
Figure 8:
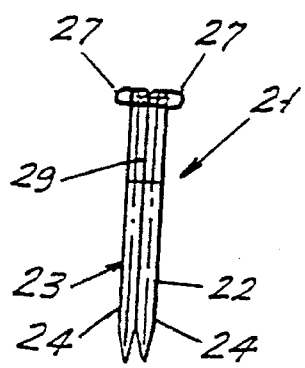
FIG. 8 is a front elevation of the clip of FIG. 7.
Figure 9:
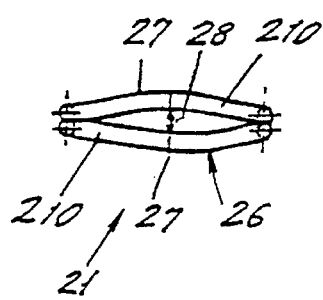
FIG. 9 is a top plan view of the clip of FIG. 7.

FIGS. 7 to 9 illustrate a third embodiment, similar to FIG. 1, formed of clip pieces 22 and 23 with legs 24 and a bridge 26 on each clip piece. The bridge 26 is formed of elongated sections 210, which, in their central part 27, have a maximum curvature producing a space 28 between the sections 210. The lower ends of the legs 24 are also tapered and/or sharpened, as indicated by the reference numeral 25.

The fundamental difference between this embodiment and that of FIG. 1 is that the bridge 26 has a stepped section 30, the purpose of which is the osteosynthesis of bones of different diameter (proximal tibia osteotomy).

As in the case of the embodiment of the figure, the legs 24 are attached along a connecting line 29.

Although the present invention has been described in relation to particular embodiments thereof, many other variations and modifications and other uses will become apparent to those skilled in the art. Therefore, the present invention should be limited not by the specific disclosure herein, but only by the appended claims.

What is claimed is:

1. A method for connecting at least two bone parts together by the application of a clip between the parts, the clip having at least two legs and two elongated bridge sections, separated, at least in part, and extending alongside each other connecting the legs, the method comprising the steps of:

placing the parts of the bone to be attached face to face and defining a connecting line between the bone parts;

providing a hole in each of said bone parts in order to receive respective legs of the clip;

positioning the clip to span across the connecting line between the two bone parts by inserting each leg in each hole; and deforming said elongated bridge sections of the clip by providing a force between the bridge sections to cause the bridge sections to move apart;

said step of deforming further causing the legs to move toward each other to bring the two bone parts together, the legs having proximal and distal portions, the distal portions being received distally in a respective hole, the distal portions of the two legs moving closer together than the proximal portions during said step of deforming.

2. A method for connecting at least two bone parts together in accordance with claim 1, wherein the insertion of the legs in each bone hole is effected by percussion.

3. A method for connecting at least two bone parts together in accordance with claim 1, wherein the clip comprises two integral clip pieces each having two legs connected by said bridge sections with corresponding legs of each clip piece being fastened together, and with the bridge sections being unconnected to each other at least in part, and further wherein said step of deforming the elongated bridge sections comprises separating said two elongated bridge sections by exerting pressure between said elongated bridge sections.

4. A method for connecting at least two bone parts together in accordance with claim 1, wherein the clip comprises two integral clip pieces each having two legs connected by said bridge sections, with corresponding legs of each clip piece being fastened together, and with the bridge sections being unconnected to each other at least in part, and further, wherein said step of deforming the elongated sections of the bridge comprises compressing and bringing said elongated bridge sections towards each other, thereby holding said bone parts together with a prescribed spacing therebetween.

* * * * *